US011610404B2

(12) United States Patent
Singhal et al.

(10) Patent No.: US 11,610,404 B2
(45) Date of Patent: Mar. 21, 2023

(54) METHODS AND SYSTEMS FOR TRACKING THE LOCATION OF A PETRI-DISH

(71) Applicant: AIRAMATRIX PRIVATE LIMITED, Thane-West (IN)

(72) Inventors: Nitin Singhal, Bangalore (IN); Satya Chaitanya Kondragunta, Mumbai (IN)

(73) Assignee: AIRAMATRIX PRIVATE LIMITED

( * ) Notice: Subject to any disclaimer, the term of this patent is extended or adjusted under 35 U.S.C. 154(b) by 0 days.

(21) Appl. No.: 17/501,552

(22) Filed: Oct. 14, 2021

(65) Prior Publication Data

US 2022/0121857 A1 Apr. 21, 2022

(30) Foreign Application Priority Data

Oct. 15, 2020 (IN) .............................. 202021044850

(51) Int. Cl.
*H04W 4/80* (2018.01)
*G06V 20/52* (2022.01)
*G06V 20/64* (2022.01)
*G06V 20/13* (2022.01)

(52) U.S. Cl.
CPC .............. *G06V 20/52* (2022.01); *G06V 20/13* (2022.01); *G06V 20/64* (2022.01); *H04W 4/80* (2018.02)

(58) Field of Classification Search
CPC combination set(s) only.
See application file for complete search history.

(56) References Cited

U.S. PATENT DOCUMENTS

| 10,528,703 | B1* | 1/2020 | Baek | H04N 1/00334 |
|---|---|---|---|---|
| 11,256,884 | B2* | 2/2022 | Roth | G06K 7/10297 |
| 2003/0078905 | A1* | 4/2003 | Haugli | G08B 26/007 |
| 2009/0237221 | A1* | 9/2009 | Battles | G06K 19/08 |
| | | | | 340/10.51 |
| 2011/0207209 | A1* | 8/2011 | Hammons | C12M 23/42 |
| | | | | 435/303.1 |
| 2014/0061306 | A1* | 3/2014 | Wu | G06K 7/10386 |
| | | | | 235/439 |
| 2015/0299639 | A1* | 10/2015 | Kleefstra | C12M 23/44 |
| | | | | 435/287.3 |
| 2017/0081707 | A1* | 3/2017 | Dillon | C12Q 1/689 |
| 2019/0191278 | A1* | 6/2019 | Singh | G06Q 50/26 |
| 2020/0088984 | A1* | 3/2020 | Haase | G02B 21/367 |
| 2021/0386580 | A1* | 12/2021 | Velis | A61F 7/0085 |

\* cited by examiner

*Primary Examiner* — Cindy Trandai
(74) *Attorney, Agent, or Firm* — Edmonds & Cmaidalka, P.C.

(57) ABSTRACT

Methods and systems for managing a petri-dish. Embodiments herein disclose a RFID tag affixed on the petri-dish, wherein the RFID tag has a thin formfactor, so as not to interfere in the use and operation of the petri-dish and a sufficiently large readability range. Embodiments herein disclose methods and systems for RFID based asset tracking of petri-dishes in a laboratory/pharmaceutical/manufacturing environment, wherein the movement of the petri-dishes are tracked automatically with minimal manual intervention.

14 Claims, 10 Drawing Sheets

METHODS AND SYSTEMS FOR TRACKING THE LOCATION OF A PETRI-DISH

CROSS REFERENCE TO RELATED APPLICATION

This application is based on and derives the benefit of Indian Provisional Application 202021044850, the contents of which are incorporated herein by reference.

TECHNICAL FIELD

Embodiments disclosed herein relate to management of petri-dishes in a laboratory/pharmaceutical/manufacturing environment and more particularly to tracking the location of petri-dishes in a laboratory/pharmaceutical/manufacturing environment.

BACKGROUND

Petri-dishes are widely used in laboratory/pharmaceutical/manufacturing environments and pass through multiple stages/areas, such as, but not limited to, sampling/exposure, sample closure, transfer to lab, incubation, generating results, and so on. Tracking the petri-dishes through all these stages manually can be cumbersome.

A solution uses a surveillance system comprising of one or more cameras to track the petri-dishes in the environment. However, such systems cannot track individual assets, suffers from occlusion threat, and requires direct line of sight. The system also comprises of multiple cameras, which are typically battery operated units, which can imbalance the clean room temperature. The system has huge storage requirements, to store the feed from the cameras and processing the feed from the camera can result in the system being slow.

A current solution for tracking petri-dishes involves the use of barcodes, wherein barcode labels are affixed on the petri-dishes and the barcode labels are scanned (as required). However, barcode scanning is done manually for each petri-dish separately.

Currently available RFID tags have readability ranges directly proportional to the thickness of the tags. So, RFID tags with high ranges (in the order of 10 feet) have typical thickness of about a few centimeters. Use of such tags on petri-dishes can interfere with the usage of the petri-dishes.

BRIEF DESCRIPTION OF FIGURES

Embodiments herein are illustrated in the accompanying drawings, through out which like reference letters indicate corresponding parts in the various figures. The embodiments herein will be better understood from the following description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve methods and systems for RFID based asset tracking and management of petri-dishes in a laboratory/pharmaceutical/manufacturing environment. Referring now to the drawings, and more particularly to FIGS. 1 through 8, where similar reference characters denote corresponding features consistently throughout the figures, there are shown embodiments.

Embodiments herein disclose a RFID tag affixed on the petri-dish, wherein the RFID tag has a thin formfactor, so as not to interfere in the use and operation of the petri-dish and a sufficiently large readability range. Embodiments herein disclose methods and systems for RFID based asset tracking of petri-dishes in a laboratory/pharmaceutical/manufacturing environment, wherein the movement of the petri-dishes are tracked automatically with minimal manual intervention.

Embodiments herein further provide a RFID tag affixed on the petri-dish, wherein the RFID tag has a thin formfactor, so as not to interfere in the use and operation of the petri-dish and a sufficiently large readability range.

Additional embodiments provided herein include methods and systems for RFID based asset tracking of petri-dishes in a laboratory, pharmaceutical, or manufacturing environment, wherein the movement and usage of the petri-dishes are tracked automatically with minimal manual intervention.

These and other aspects of the embodiments herein will be better appreciated and understood when considered in conjunction with the following description and the accompanying drawings. It should be understood, however, that the following descriptions, while indicating at least one embodiment and numerous specific details thereof, are given by way of illustration and not of limitation. Many changes and modifications may be made within the scope of the embodiments herein without departing from the spirit thereof, and the embodiments herein include all such modifications.

Each petri-dish can have a Radio Frequency Identification (RFID) tag affixed to it. The RFID can be of a minimal thickness, so as not to interfere in the normal use and operation of the petri-dish in the laboratory/pharmaceutical/manufacturing environment. In an embodiment herein, the RFID tag can be of a sticker form and can be present on the surface of the petri-dish. The RFID tag can be at least one of an active tag, a passive tag or a battery-assisted passive tag. The RFID tag can be a high-frequency tag, wherein the RFID tag has a high readability range. In an example herein, the readability range of the RFID tag is 10 feet. In an embodiment herein, the RFID tag can be in the form of a sticker attached to a surface of the petri-dish. In an embodiment herein, the RFID tag can be inbuilt into the petri-dish. In an example herein, the RFID tag can be a thin film.

Each tag can have a unique identification means (such as a numerical code, an alphanumerical code, and so on), which can be used to uniquely identify the petri-dish. The RFID tags can be programmed with information such as the unique identifier, current contents of the petri-dish and additional information related to the contents, usage history of the petri-dish, persons associated with the petri-dish, locations where the petri-dish can be used, information present in a tracking tag associated with the petri-dish, and so on.

In an example, the environment comprises of a clean room, a laboratory and an incubation area. The petri-dishes move across these locations. Each of these locations can comprise of one or more RFID readers. The RFID readers can be at least one of an active reader, and/or a passive reader and can depend on the type of RFID tags affixed to the petri-dishes. The readers can read the RFID tags in their respective locations and provide the RFID tag to a server and/or a device, which can comprise an application. The application can track the locations of the petri-dishes across the environment. The application can store the determined locations in a suitable location, such as, but not limited to, an internal memory, a database, a file server, a data server, the Cloud, and so on.

Figure 1:
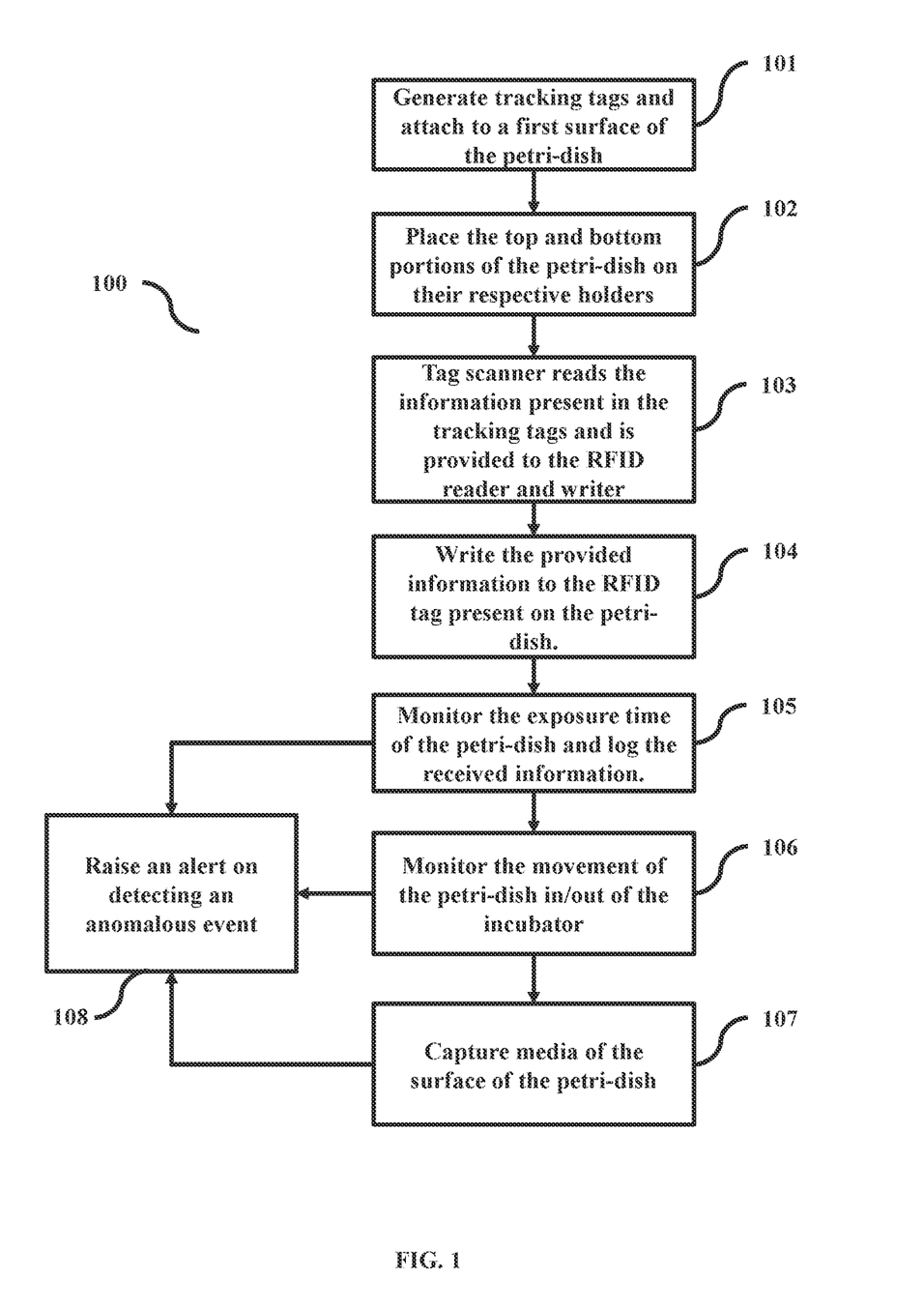
FIG. 1 is a flow diagram depicting the process of tracking and managing a petri-dish in a laboratory/pharmaceutical/manufacturing environment, according to embodiments as disclosed herein.
Figure 2A:
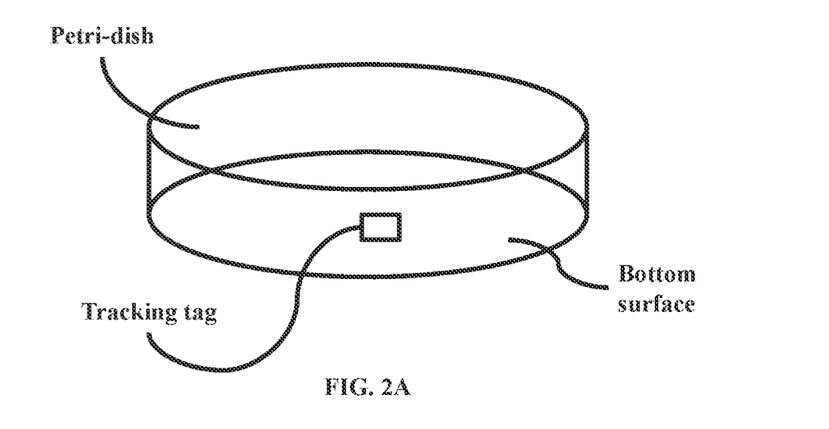
FIGS. 2A, 2B, 2C and 2D depict example placements of the tracking tag on the petri-dish, according to embodiments as disclosed herein.
Figure 2B:
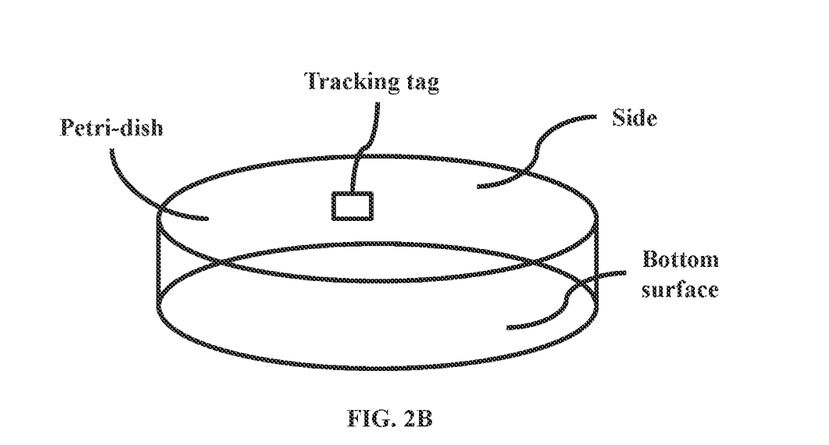
Figure 2C:
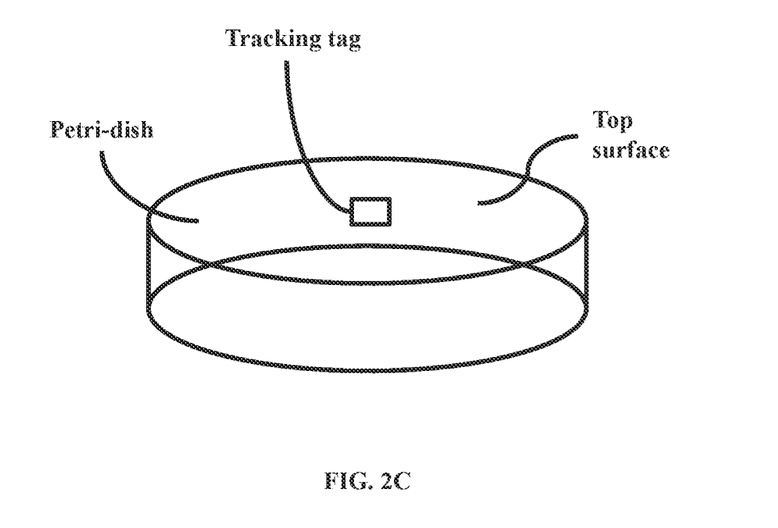
Figure 2D:
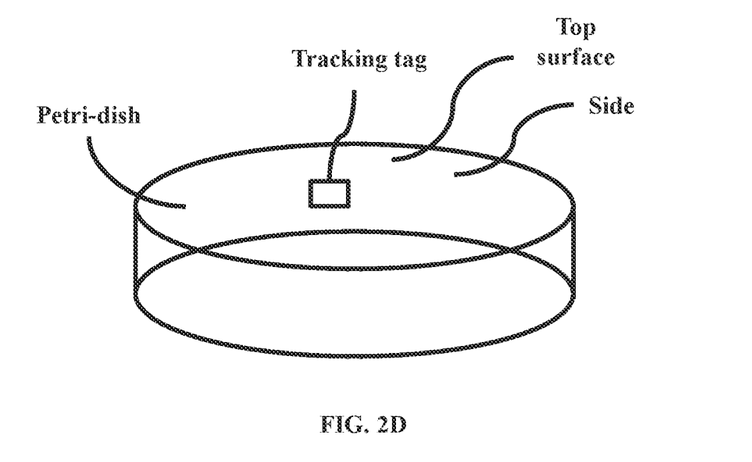
Figure 3A:
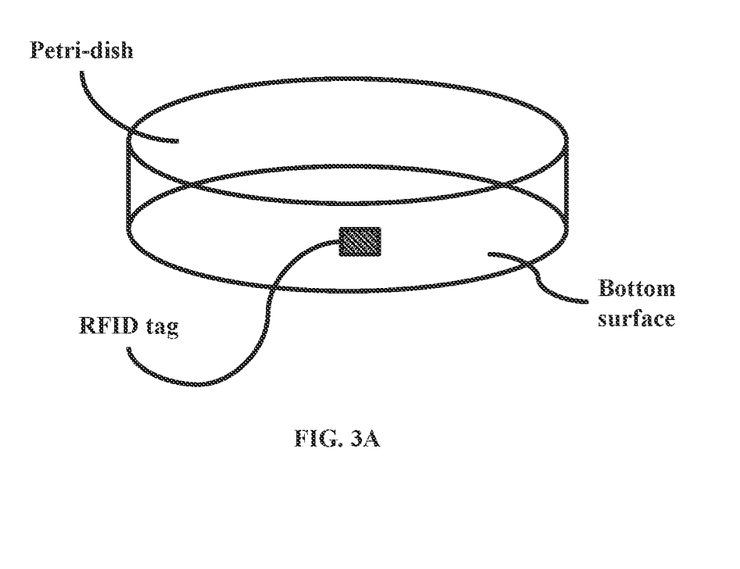
FIGS. 3A, 3B, 3C and 3D depict example placements of the RFID tag on the petri-dish, according to embodiments as disclosed herein.
Figure 3B:
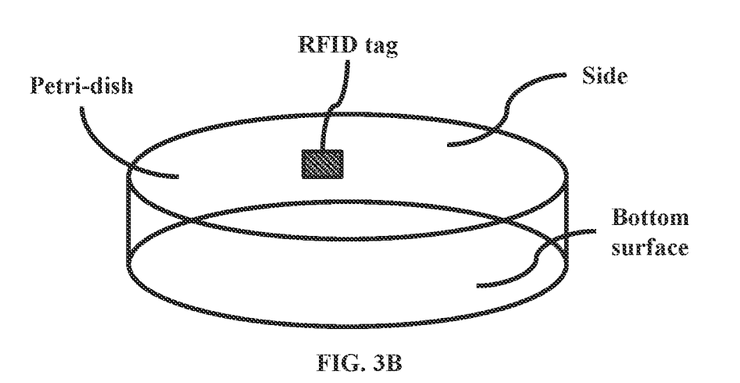
Figure 3C:
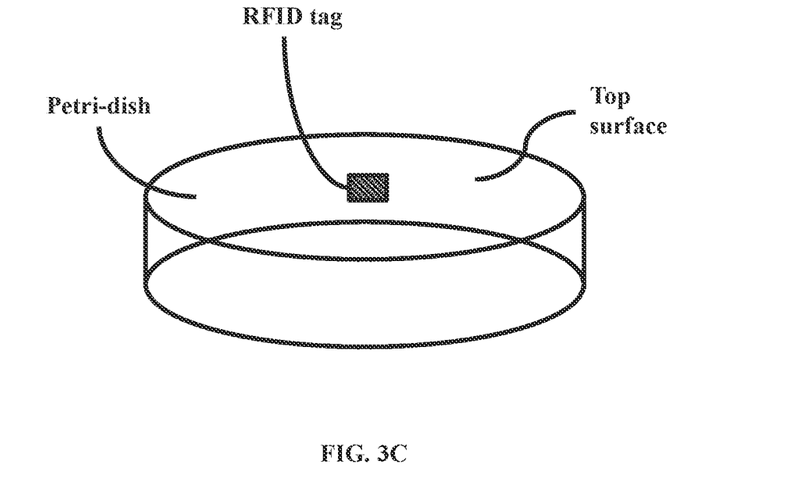
Figure 3D:
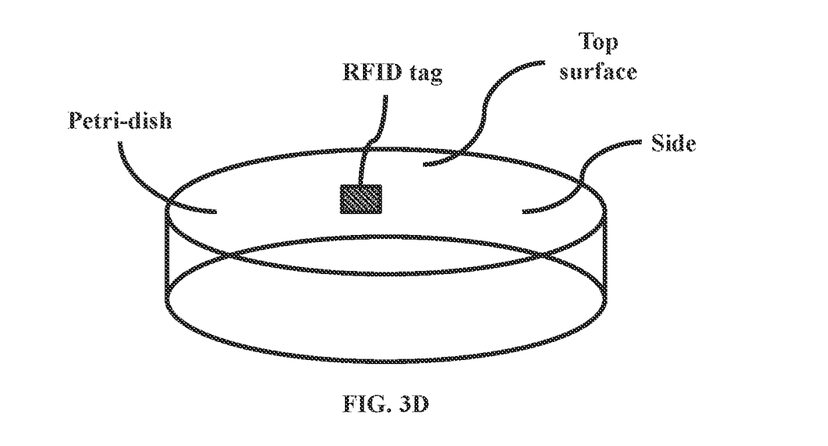

FIG. 1 is a flow diagram depicting the process of tracking and managing a petri-dish in a laboratory/pharmaceutical/manufacturing environment. In step 101, tracking tags are generated for a specific petri-dish and affixed to a first surface of the petri-dish. Examples of the tracking tags can be barcodes, RFID, Near Field Communication (NFC), and so on. Further, RFID tags are affixed to a second surface of the petri-dish. The tracking tags can contain information such as, but not limited to, date & time stamps of generating the tracking tags, persons related to managing and/or supervising the petri-dish during the journey of the petri-dish across the environment, expected exposure time, expected time that the petri-dish has to spend in the incubator, and so on. In an embodiment herein, the first surface of the petri-dish can be on the bottom portion of the petri-dish, wherein the tracking tag is affixed to one surface of the bottom portion of the petri-dish; i.e., on the bottom surface of the petri-dish or on a side of the bottom portion of the petri-dish, as depicted in the examples in FIGS. 2A and 2B respectively. In an embodiment herein, the first surface of the petri-dish can be on the top portion of the petri-dish, wherein the tracking tag is affixed to one surface of the top portion of the petri-dish; i.e., on the top surface of the petri-dish or on a side of the top portion of the petri-dish, as depicted in the examples in FIGS. 2C and 2D respectively. In an embodiment herein, the second surface of the petri-dish can be on the bottom portion of the petri-dish, wherein the RFID is affixed to one surface of the bottom portion of the petri-dish; i.e., on the bottom surface of the petri-dish or on a side of the bottom portion of the petri-dish, as depicted in the examples in FIGS. 3A and 3B respectively. In an embodiment herein, the second surface of the petri-dish can be on the top portion of the petri-dish, wherein the RFID is affixed to one surface of the top portion of the petri-dish; i.e., on the top surface of the petri-dish or on a side of the top portion of the petri-dish, as depicted in the examples in FIGS. 3C and 3D respectively. Embodiments herein further refer to the surface of the petri-dish to which the tracking tag is affixed as the tag surface. Embodiments herein further refer to the surface of the petri-dish to which the RFID tag is affixed as the RFID surface.

Once the petri-dish has been prepared, in step 102, the top and bottom portions of the petri-dish are placed on their respective holders. A tag scanner is placed in a position so as to read the tracking tag present on the first surface of the petri-dish. Consider that the tracking tag is attached to the bottom portion of the petri-dish, the bottom portion of the petri-dish is placed on the holder in proximity to the tag scanner. Consider that the tracking tag is attached to the top portion of the petri-dish, the top portion of the petri-dish is placed on the holder in proximity to the tag scanner. A RFID writer and reader is placed in a position so as to read and write to the RFID tag present on the second surface of the petri-dish. Consider that the RFID is attached to the bottom portion of the petri-dish, the bottom portion of the petri-dish is placed on the holder in proximity to the RFID writer and reader. Consider that the RFID is attached to the top portion of the petri-dish, the top portion of the petri-dish is placed on the holder in proximity to the RFID writer and reader.

In step 103, the scanner reads the information present in the tracking tag and the read information is provided to the RFID writer and reader. In an embodiment herein, the tag scanner can provide the read information to the RFID writer and reader directly, using at least one of a wired means or a wireless means. In an embodiment herein, the tag scanner can provide the read information to the RFID writer and reader via a petri-dish management system, using at least one of a wired means or a wireless means.

In step 104, the RFID writer and reader writes the provided information to the RFID tag present on the petri-dish.

In step 105, the petri-dish management module monitors the exposure time of the petri-dish using information send from the tag scanner and the RFID writer and reader and logs the received information. The tag scanner and the RFID writer and reader continuously monitor the respective surfaces of the petri-dish and send the monitored information to the petri-dish management module using at least one of a wired means or a wireless means. The petri-dish management module can consider that the contents of the petri-dish are being exposed, if the top and bottom portions of the petri-dish are present on their respective holders. In an embodiment herein, the petri-dish can be passive air sampled. In an embodiment herein, the petri-dish can be active air sampled.

Consider that the petri-dish has been moved to the incubator, in step 106, the petri-dish management module monitors the movement of the petri-dish in/out of the incubator, using one or more RFID readers located around the incubator, such that the RFID reader can read RFIDs moving in/out of the incubator. The petri-dish management module logs the movement of the petri-dish with respect to the incubator.

Consider that the petri-dish is being inspected, in step 107, the petri-dish management module can use a camera to capture one or media of the surface of the petri-dish. The petri-dish management module can log the captured media.

On detecting any anomalous event, in step 108, the petri-dish management module can provide at least one alert and log the alert with corresponding conditions (such as details of the detected anomalous event(s), time stamps, and so on). Examples of the anomalous event can be, the petri-dish not being exposed for the correct exposure time (either less than the expected correct exposure time or greater than the expected correct exposure time), the petri-dish not being incubated in the incubator for the correct time, and so on. The alert can be at least one of an audio alert, a visual alert, a message (an email, a Short Messaging Service (SMS), an instant message, and so on), and so on.

The various actions in method 100 may be performed in the order presented, in a different order or simultaneously. Further, in some embodiments, some actions listed in FIG. 1 may be omitted.

Figure 4:
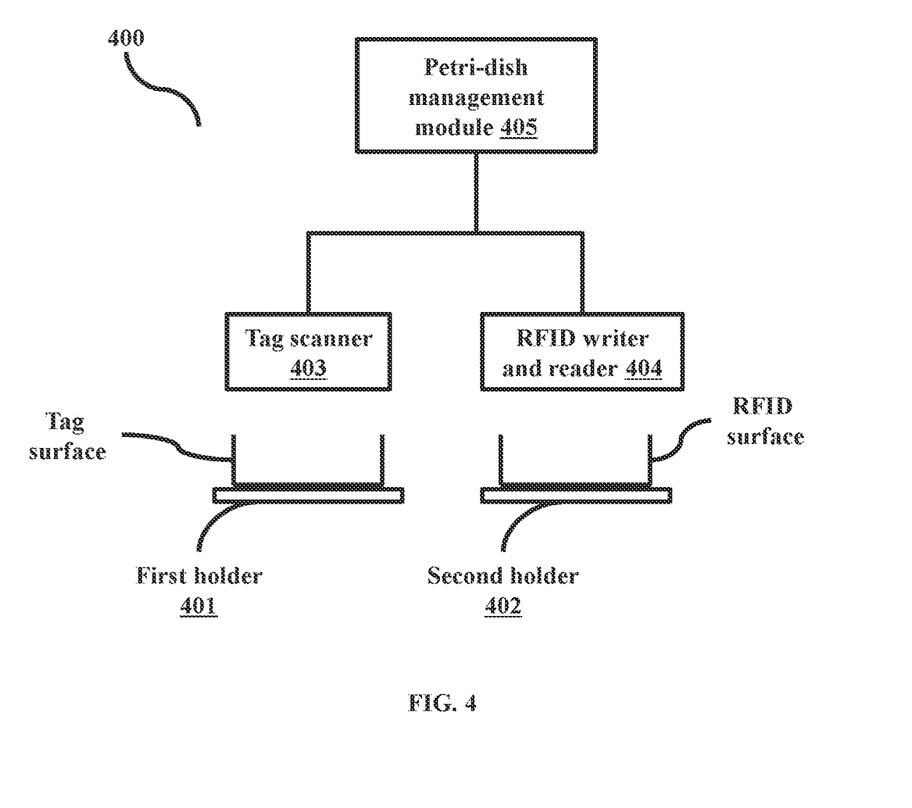
FIG. 4 depicts a system for writing information to the RFID tag and monitoring the exposure time of the petri-dish, according to embodiments as disclosed herein, according to embodiments as disclosed herein.

FIG. 4 depicts a system for writing information to the RFID tag and monitoring the exposure time of the petri-dish, according to embodiments as disclosed herein. The system 400, as depicted, comprises the first holder 401, the second holder 402, the tag scanner 403, the RFID writer and reader 404, and the petri-dish management system 405. In an embodiment herein, the system 400 can enable the petri-dish to be passive air sampled. In an embodiment herein, the system can enable the petri-dish to be active air sampled.

Consider that the tag surface of the petri-dish is placed on the first holder 401. The tag scanner 403 is placed in proximity to the first holder 401, such that the tag scanner 403 can read the tracking tag present on the tag surface of the petri-dish.

Consider that the RFID surface of the petri-dish is placed on the second holder 402. The RFID writer and reader 404 is placed in proximity to the second holder 402, such that the RFID writer and reader 404 can read the RFID on the RFID surface of the petri-dish.

The tag scanner 403 and the petri-dish management system 405 can communicate with each other using at least one of a wired means or a wireless means. Examples of the wired means can be Local Area Network (LAN), Universal Serial Bus (USB), USB-C, micro USB, mini USB, USB-B, Ethernet, Controller Area Network (CAN), and so on. Examples of the wireless means can be Wi-Fi, a cellular network, Bluetooth, Wi-Fi Direct, and so on.

The RFID writer and reader 404 and petri-dish management system 405 can communicate with each other using at least one of a wired means or a wireless means. Examples of the wired means can be Local Area Network (LAN), Universal Serial Bus (USB), USB-C, micro USB, mini USB, USB-B, Ethernet, Controller Area Network (CAN), and so on. Examples of the wireless means can be Wi-Fi, a cellular network, Bluetooth, Wi-Fi Direct, and so on.

The tag scanner 403 and the RFID writer and reader 404 can communicate with each other using at least one of a wired means or a wireless means. Examples of the wired means can be Local Area Network (LAN), Universal Serial Bus (USB), USB-C, micro USB, mini USB, USB-B, Ethernet, Controller Area Network (CAN), and so on. Examples of the wireless means can be Wi-Fi, a cellular network, Bluetooth, Wi-Fi Direct, and so on.

On detecting that a petri-dish has been placed on the first holder 401, the tag scanner 403 can read the information present in the tracking tag. The tag scanner 403 can provide the read information to the RFID writer and reader 404. In an embodiment herein, the tag scanner 403 can provide the read information to the RFID writer and reader 404 directly. In an embodiment herein, the tag scanner 403 can provide the read information to the RFID writer and reader 404, via the petri-dish management system 405. On receiving the read information, the RFID writer and reader 404 can write the provided information to the RFID tag.

The tag scanner 403 and the RFID writer and reader 404 can monitor the presence of the respective surfaces of the petri-dish on the respective holders by monitoring the presence of the tracking tag by the tag scanner 403 on the tag surface and the presence of the RFID tag by the RFID writer and reader 404 on the RFID surface. The tag scanner 403 can communicate the monitored information to the petri-dish management system 405, including the presence of the tag surface (by detecting the presence of the tracking tag on the tag surface). The RFID writer and reader 404 can communicate the monitored information to the petri-dish management system 405, including the presence of the RFID surface (by detecting the presence of the RFID tag on the RFID surface).

The petri-dish management system 405 can monitor if the petri-dish is being exposed for the correct exposure time, by ensuring that the tag surface is present on the first holder 401 (based on information provided by the tag scanner 403) and the RFID surface is present on the second holder 402 (based on information provided by the RFID writer and reader 404). In an embodiment herein, the correct exposure time can be configured by an authorized person. In an embodiment herein, the correct exposure time can be determined by the petri-dish management system 405, based on previous history and information related to the petri-dish being exposed (which can be information provided by the tag scanner 403 and read from the tracking tag present on the petri-dish). The petri-dish management system 405 can log the received information in a suitable location (such as, but not limited to, an internal memory, a data server, the Cloud, a file server, an expandable memory, and so on).

On detecting that the petri-dish has not been exposed for the correct exposure time (on detecting that the tag surface is not present on the first holder 401 (based on information provided by the tag scanner 403) or the RFID surface is not present on the second holder 402 (based on information provided by the RFID writer and reader 404)), the petri-dish management system 405 can raise an alert. The alert can be at least one of an audio alert, a visual alert, a message (an email, a Short Messaging Service (SMS), an instant message, and so on), and so on.

The tag scanner 403 can communicate additional information to the petri-dish management system 405, wherein examples of the additional information can be battery levels of the tag scanner 403, status of the tag scanner 403, a connectivity status of the tag scanner 403, and so on.

The RFID writer and reader 404 can communicate additional information to the petri-dish management system 405, wherein examples of the additional information can be battery levels of the RFID writer and reader 404, status of the RFID writer and reader 404, a connectivity status of the RFID writer and reader 404, and so on.

In an embodiment herein, the system 400 can comprise of one or more cameras, wherein the field of view of the camera includes the first holder 401 and the second holder 402. The camera can capture media (which can be at least one of video, images, and so on) and provide the captured media to the petri-dish management system 405, along with the respective timestamps. The petri-dish management system 405 can determine the exposure time of the petri-dish based on the open/close state of the petri-dish and the timestamps.

Figure 5:
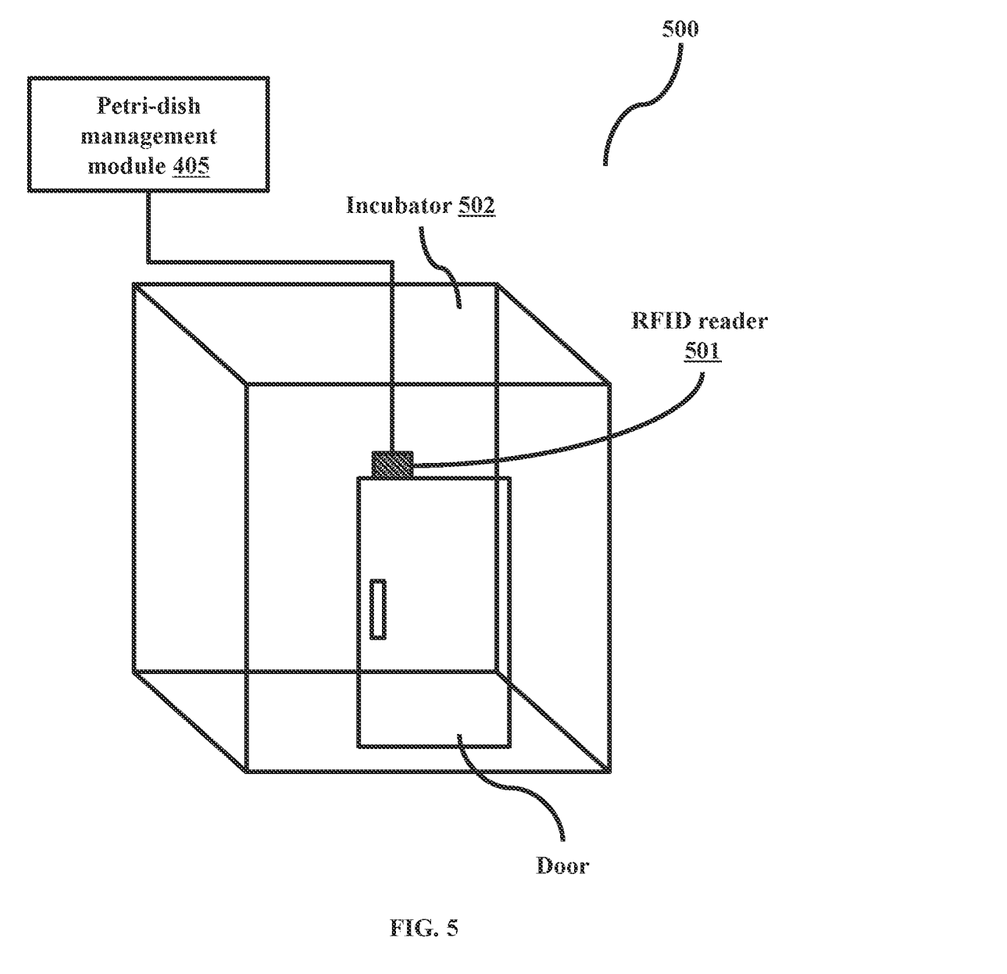
FIG. 5 depicts a system for monitoring the incubation of a petri-dish, according to embodiments as disclosed herein, according to embodiments as disclosed herein.

FIG. 5 depicts a system for monitoring the incubation of a petri-dish, according to embodiments as disclosed herein. The system 500, as depicted comprises of one or more RFID readers 501, and the petri-dish management system 405, wherein the RFID readers 501 can be placed around the door(s) of an incubator 502. This enables the RFID readers to read the RFID tags present on any petri-dish that moves in and out of the incubator 502. In an embodiment herein, the petri-dish management system 405 can communicate with multiple RFID readers present on multiple incubators.

The RFID reader 501 can communicate with the petri-dish management system 405 using at least one of a wired means or a wireless means. Examples of the wired means can be Local Area Network (LAN), Universal Serial Bus (USB), USB-C, micro USB, mini USB, USB-B, Ethernet, Controller Area Network (CAN), and so on. Examples of the wireless means can be Wi-Fi, a cellular network, Bluetooth, Wi-Fi Direct, and so on.

The RFID reader 501, on detecting that a RFID tag (which is present on the petri-dish) has moved in or out of the incubator, can communicate the information present in the RFID tag to the petri-dish management system 405, along with the corresponding timestamps. On receiving the information and the timestamps from the RFID reader 501, the petri-dish management system 405 can log the received information and the timestamps. A first entry in the log for the RFID tag can be determined as the petri-dish entering the incubator 502, with a second entry in the log for the RFID tag can be determined as the petri-dish leaving the incubator 502. The petri-dish management system 405 can determine the time between the first entry and the second entry, as the time for which the petri-dish has been incubated. The petri-dish management system 405 can log the received information in a suitable location (such as, but not limited to, an internal memory, a data server, the Cloud, a file server, an expandable memory, and so on).

The petri-dish management system 405 can determine that the petri-dish has been incubated for the correct incubation time, by ensuring that the petri-dish is present inside the incubator for the correct incubation time (based on information provided by the RFID reader 501). In an embodiment herein, the correct incubation time can be configured by an authorized person. In an embodiment herein, the correct incubation time can be determined by the petri-dish management system 405, based on previous history and information related to the petri-dish being incubated (which can be information provided by the tag scanner 403 and read from the tracking tag present on the petri-dish).

On detecting that the petri-dish has not been incubated for the correct incubation time (on detecting that the petri-dish has not been present inside the incubator for the correct incubation time), the petri-dish management system 405 can raise an alert. The alert can be at least one of an audio alert, a visual alert, a message (an email, a Short Messaging Service (SMS), an instant message, and so on), and so on.

The RFID reader 501 can communicate additional information to the petri-dish management system 405, wherein examples of the additional information can be battery levels of the RFID reader 501, status of the RFID reader 501, a connectivity status of the RFID reader 501, and so on.

Figure 6:
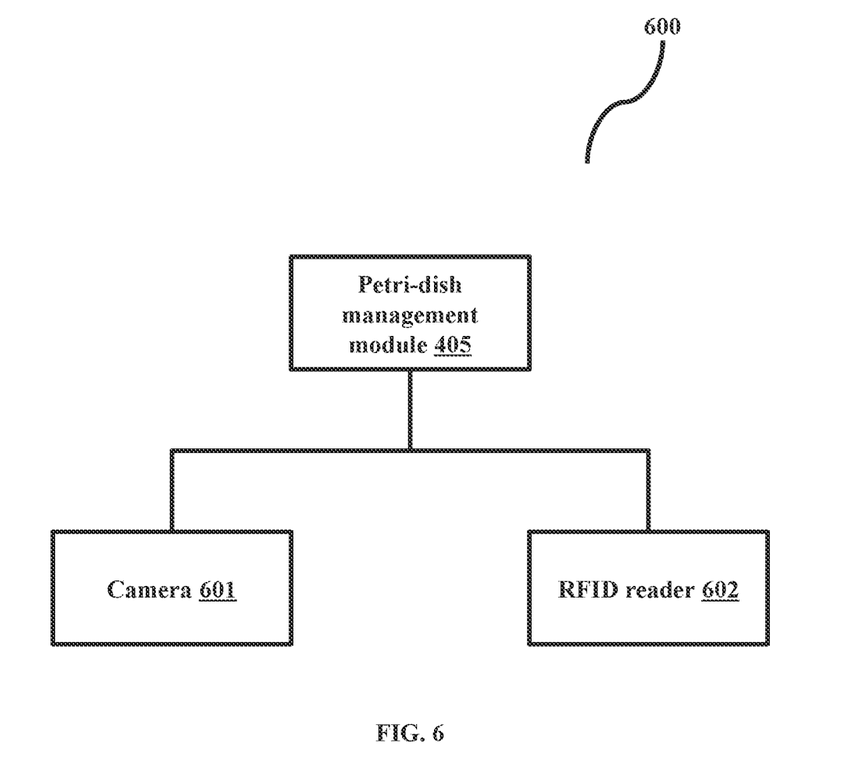
FIG. 6 depicts a system for capturing the surface of the petri-dish, according to embodiments as disclosed herein, according to embodiments as disclosed herein.

FIG. 6 depicts a system for capturing the surface of the petri-dish, according to embodiments as disclosed herein. The system 600 comprises of at least one camera 601 and a RFID reader 602, connected to the petri-dish management system 405. The camera 601 can be configured to capture at least one media of the surface of the petri-dish. The captured media can be at least one of an image, a video, an animation, and so on.

The camera 601 can communicate with the petri-dish management system 405 using at least one of a wired means or a wireless means. Examples of the wired means can be Local Area Network (LAN), Universal Serial Bus (USB), USB-C, micro USB, mini USB, USB-B, Ethernet, Controller Area Network (CAN), and so on. Examples of the wireless means can be Wi-Fi, a cellular network, Bluetooth, Wi-Fi Direct, and so on. In an embodiment herein, the camera 601 can be inbuilt into the petri-dish management system 405. The camera 601 can communicate the captured information to the petri-dish management system 405.

The RFID reader 602 can communicate with the petri-dish management system 405 using at least one of a wired means or a wireless means. Examples of the wired means can be Local Area Network (LAN), Universal Serial Bus (USB), USB-C, micro USB, mini USB, USB-B, Ethernet, Controller Area Network (CAN), and so on. Examples of the wireless means can be Wi-Fi, a cellular network, Bluetooth, Wi-Fi Direct, and so on. The RFID reader 602 can read the RFID tag attached to the petri-dish and communicate the read information to the petri-dish management system 405.

The petri-dish management system 405 can log the received media and the received information in a suitable location (such as, but not limited to, an internal memory, a data server, the Cloud, a file server, an expandable memory, and so on).

The camera 601 can communicate additional information to the petri-dish management system 405, wherein examples of the additional information can be battery levels of the camera 601, status of the camera 601, a connectivity status of the camera 601, and so on.

The RFID reader 602 can communicate additional information to the petri-dish management system 405, wherein examples of the additional information can be battery levels of the RFID reader 602, status of the RFID reader 602, a connectivity status of the RFID reader 602, and so on.

The petri-dish management system 405 can perform at least one action on the received media. Examples of the action can be performing classification of the media (using a deep learning classifier), counting the colonies present in the petri-dish using the received media (using a colony counter method and system, as disclosed in IN202021001509).

Further, using the media captured by the camera 601, the petri-dish management system 405 can determine whether the petri-dish is in open/close state. The petri-dish management system 405 can compare the media received from the camera 601 to previously acquired sample media of petri-dishes in open and closed states, wherein the sample media is of petri-dishes in similar condition (including the exposure time, incubation time, type of colony/sample present in the petri-dish, and so on) to the petri-dish, whose media is currently being captured.

Figure 7:
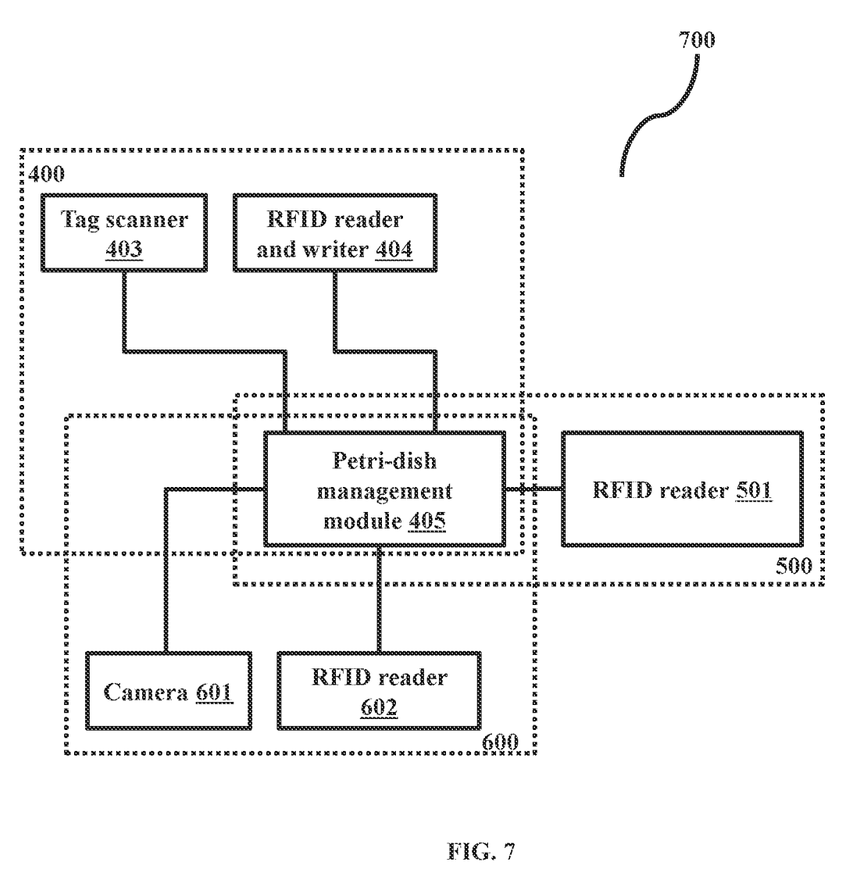
FIG. 7 depicts the system comprising of the petri-dish management system connected to the other modules and entities, according to embodiments as disclosed herein.

FIG. 7 depicts the system 700 comprising of the petri-dish management system connected to the other modules and entities. Examples of the other modules can be, such as the tag scanner 403, the RFID writer and reader 404, the RFID readers 501, 602, the camera 601, and so on. In an embodiment herein, the petri-dish management system 405 can be connected to other entities, such as, the Cloud, a file server, a data server, and so on. In an embodiment herein, the petri-dish management system 405 can be located remotely from one or more of the other modules. The petri-dish management system 405 can communicate with the other modules and/or the other entities using at least one of a wired means or a wireless means. Examples of the wired means can be Local Area Network (LAN), Universal Serial Bus (USB), USB-C, micro USB, mini USB, USB-B, Ethernet, Controller Area Network (CAN), and so on. Examples of the wireless means can be Wi-Fi, a cellular network, Bluetooth, Wi-Fi Direct, and so on. In an embodiment herein, the petri-dish management system 405 can be co-located with one or more of the other modules.

Figure 8:
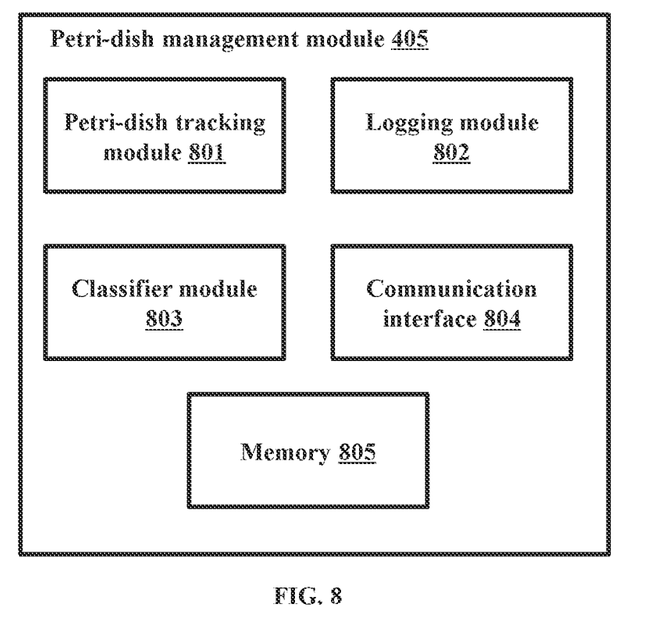
FIG. 8 depicts the petri-dish management module, according to embodiments as disclosed herein.

FIG. 8 depicts the petri-dish management module. The petri-dish management system 405, as depicted, comprises a petri-dish tracking module 801, a logging module 802, a classifier module 803, at least one communication interface 804, and a memory 805.

The petri-dish management system 405 may include one or a plurality of processors. The one or a plurality of processors may be a general-purpose processor, such as a central processing unit (CPU), an application processor (AP), or the like, a graphics-only processing unit such as a graphics processing unit (GPU), a visual processing unit (VPU), and/or an Artificial Intelligence (AI)-dedicated processor (such as a neural processing unit (NPU)). The one or a plurality of processors may be a single processer, a plurality of processors, multiple homogeneous or heterogeneous cores, multiple Central Processing Units (CPUs) of different kinds, microcontrollers, and so on.

The communication interface 804 may include one or more components which enables the petri-dish management system 405 to communicate with the one or more external devices/modules/entities using communication methods that have been supported by the communication network. The communication interface 804 may include the components such as, a wired communicator, a short-range communicator, a mobile/wireless communicator, and a broadcasting receiver. The wired communicator may enable the petri-dish management system 405 to communicate with the external devices using the communication methods such as, but are not limited to, wired LAN, the Ethernet, and so on. The short-range communicator may enable the petri-dish management system 405 to communicate with the external devices using the communication methods such as, but are not limited to, Bluetooth low energy (BLE), near field communicator (NFC), WLAN (or Wi-fi), Zigbee, infrared data association (IrDA), Wi-Fi direct (WFD), UWB communication, Ant+ (interoperable wireless transfer capability) communication, shared wireless access protocol (SWAP), wireless broadband internet (Wibro), wireless gigabit alliance (WiGiG), and so on.

The memory 805 may store at least one of, one or more applications, information received from the other modules, configured information (for example, the correct exposure time, the correct incubation time, sample media of the surface of incubated petri-dishes, and so on), and so on. The memory 805 referred herein may include at least one type of storage medium, from among a flash memory type storage medium, a hard disk type storage medium, a multi-media card micro type storage medium, a card type memory (for example, an SD or an XD memory), random-access memory (RAM), static RAM (SRAM), read-only memory (ROM), electrically erasable programmable ROM (EEPROM), programmable ROM (PROM), a magnetic memory, a magnetic disk, or an optical disk.

The petri-dish tracking module 801 can receive information from other modules, through the communication interface 804. Examples of the other modules can be, but not limited to, the tag scanner 403, a RFID writer and reader 404, RFID readers 501, 602, the camera 601, and so on.

The petri-dish tracking module 801 can receive information read by the tag scanner 403, through the communication interface 804. The petri-dish tracking module 801 can forward the received information to the RFID writer and reader 404.

The petri-dish tracking module 801 can receive information read by the tag scanner 403 and the RFID writer and reader 404 in real time. The petri-dish tracking module 801 can determine that the tracking tag and RFID portions of the petri-dishes are still present on the respective holders 401, 402, by detecting that information is being received in real-time from the tag scanner 403 and the RFID writer and reader 404. If information is not received from the tag scanner 403 or the RFID writer and reader 404, the petri-dish tracking module 801 can determine that either one of tracking tag portion or the RFID portion is not present in their respective holders, and if the petri-dish has not been exposed for the correct exposure time, the petri-dish tracking module 801 raises an alert accordingly. The alert can be at least one of an audio alert, a visual alert, a message (an email, a Short Messaging Service (SMS), an instant message, and so on), and so on. The logging module 802 can log the information received from the tag scanner 403 and the RFID writer and reader 404 in real time along with the timestamps, wherein the information can be logged in at least one of the memory 805 or any other suitable location.

The petri-dish tracking module 801 can receive information read by the RFID reader 501 in real time. A first entry in the log for the RFID tag can be determined by the petri-dish tracking module 801 as the petri-dish entering the incubator 502, with a second entry in the log for the RFID tag can be determined by the petri-dish tracking module 801 as the petri-dish leaving the incubator 502. The petri-dish tracking module 801 can determine the time between the first entry and the second entry, as the time for which the petri-dish has been incubated. The petri-dish tracking module 801 can determine that the petri-dish has been incubated for the correct incubation time, by ensuring that the petri-dish is present inside the incubator for the correct incubation time (based on information provided by the RFID reader 501). If the petri-dish has not been exposed for the correct exposure time, the petri-dish tracking module 801 raises an alert accordingly. The alert can be at least one of an audio alert, a visual alert, a message (an email, a Short Messaging Service (SMS), an instant message, and so on), and so on. The logging module 802 can log the information received from the RFID reader 501 in real time along with the timestamps, wherein the information can be logged in at least one of the memory 805 or any other suitable location.

The petri-dish tracking module 801 can receive media captured by the camera 601 and the information read by the RFID reader 602 in real time. The classifier module 803 can perform at least one action on the received media. Examples of the action can be performing classification of the media (using a deep learning classifier), counting the colonies present in the petri-dish using the received media (using a colony counter method and system, as disclosed in IN202021001509). The logging module 802 can log the information received from the camera 601 and the RFID reader 602 in real time along with the timestamps, wherein the information can be logged in at least one of the memory 805 or any other suitable location.

In an embodiment herein, the petri-dish management system 405 comprises a user interface, which enables an authorized user to track and manage the petri-dishes. The user interface can enable the authorized user to access the logged information. The user interface can enable the authorized user to provide information such as the correct exposure time, correct incubation time, and so on.

The embodiments disclosed herein can be implemented through at least one software program running on at least one hardware device and performing network management functions to control the network elements. The elements shown in FIGS. 4, 5, 6, 7, and 8 include blocks which can be at least one of a hardware device, or a combination of hardware device and software module.

The embodiment disclosed herein describes methods and systems for RFID based asset tracking of petri-dishes in a laboratory/pharmaceutical environment. Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in at least one embodiment through or together with a software program written in e.g. Very high speed integrated circuit Hardware Description Language (VHDL) another programming language, or implemented by one or more VHDL or several software modules being executed on at least one hardware device. The hardware device can be any kind of portable device that can be programmed. The device may also include means which could be e.g. hardware means like e.g. an ASIC, or a combination of hardware and software means, e.g. an ASIC and an FPGA, or at least one microprocessor and at least one memory with software modules located therein. The method embodiments described herein could be implemented partly in hardware and partly in software. Alternatively, the invention may be implemented on different hardware devices, e.g. using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the scope of the embodiments as described herein.

We claim:

1. A method (100) for managing a petri-dish, the method comprising
monitoring (105), by a petri-dish management system (405), exposure time of the petri-dish using information provided by a tag scanner (403) and a Radio Frequency Identification (RFID) writer and reader (404), wherein the tag surface and the RFID surface are present on a first holder (401) and a second holder (402) respectively and monitored by the tag scanner (403) using a tracking tag present on the tag surface and the RFID writer and reader (404) using a RFID tag present on the RFID surface respectively; and
monitoring (106), by the petri-dish management system (405), incubation time of the petri-dish in an incubator (501) using information provided by a RFID reader (502), wherein the RFID reader (502) monitors movement of the petri-dish in/out of the incubator (501) using the RFID tag.

2. The method, as claimed in claim 1, wherein the method further comprises of writing (104), by the RFID writer and reader (404), information to the RFID tag present on the RFID surface of the petri-dish, wherein the information is present on the tracking tag present on the tag surface of the petri-dish.

3. The method, as claimed in claim 1, wherein the petri-dish is at least one of active air sampled and passive air sampled.

4. The method, as claimed in claim 1, wherein the method comprises of raising (108) an alert, by the petri-dish management system (405), on detecting at least one anomalous event.

5. The method, as claimed in claim 1, wherein the method further comprises
capturing (107) at least one media, by a camera (601), of a top surface of the petri-dish; and
performing, the petri-dish management system (405), classification of the media.

6. The method, as claimed in claim 5, wherein the method further comprises determining, by the petri-dish management system (405), the open/close state of the petri-dish by comparing the media captured by the camera (601) to sample media.

7. The method, as claimed in claim 1, wherein the method further comprises logging, by the petri-dish management system (405), information received from the tag scanner (403), the RFID writer and reader (404), the RFID scanner (501), a RFID scanner (602), the camera (601), timestamps of the received data and information related to the petri-dish.

8. A petri-dish management system (405) configured for:
monitoring exposure time of the petri-dish using information provided by a tag scanner (403) and a Radio Frequency Identification (RFID) writer and reader (404), wherein the tag surface and the RFID surface are present on a first holder (401) and a second holder (402) respectively and monitored by the tag scanner (403) using a tracking tag present on the tag surface and the RFID writer and reader (404) using a RFID tag present on the RFID surface respectively; and
monitoring incubation time of the petri-dish in an incubator (501) using information provided by a RFID reader (502), wherein the RFID reader (502) monitors movement of the petri-dish in/out of the incubator (501).

9. The petri-dish management module, as claimed in claim 8, wherein the petri-dish management system (405) is further configured to write information to the RFID tag present on the RFID surface of the petri-dish using a RFID writer and reader (404), wherein the information is present on the tracking tag present on the tag surface of the petri-dish.

10. The petri-dish management module, as claimed in claim 8, wherein the petri-dish is at least one of active air sampled and passive air sampled.

11. The petri-dish management module, as claimed in claim 8, wherein the petri-dish management system (405) is further configured to raise an alert, by the petri-dish management system (405), on detecting at least one anomalous event.

12. The petri-dish management module, as claimed in claim 8, wherein the petri-dish management system (405) is further configured to classify at least one media, wherein the at least one media is captured by a camera (601) of a top surface of the petri-dish.

13. The petri-dish management module, as claimed in claim 12, wherein the petri-dish management system (405) is further configured to determine an open/close state of the petri-dish by comparing the media captured by the camera (601) to sample media.

14. The petri-dish management module, as claimed in claim 8, wherein the petri-dish management system (405) is further configured to log information received from the tag scanner (403), the RFID writer and reader (404), the RFID scanner (501), a RFID scanner (602), the camera (601), timestamps of the received data and information related to the petri-dish.

\* \* \* \* \*